United States Patent
Morris et al.

(10) Patent No.: US 10,034,667 B2
(45) Date of Patent: Jul. 31, 2018

(54) APPARATUS AND METHOD FOR HEART VALVE REPAIR

(71) Applicant: St. Jude Medical, Cardiology Division, Inc., St. Paul, MN (US)

(72) Inventors: Benjamin E. Morris, Jeffersonville, IN (US); Mark Griffin, Louisville, KY (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 418 days.

(21) Appl. No.: 14/193,906

(22) Filed: Feb. 28, 2014

(65) Prior Publication Data

US 2014/0243860 A1    Aug. 28, 2014

Related U.S. Application Data

(60) Provisional application No. 61/770,612, filed on Feb. 28, 2013.

(51) Int. Cl.
*A61B 17/10* (2006.01)
*A61F 2/24* (2006.01)
*A61B 17/068* (2006.01)
*A61B 17/064* (2006.01)
*A61B 17/29* (2006.01)
*A61B 17/00* (2006.01)

(52) U.S. Cl.
CPC ...... *A61B 17/0684* (2013.01); *A61B 17/0644* (2013.01); *A61B 17/29* (2013.01); *A61B 2017/00243* (2013.01); *A61B 2017/00783* (2013.01); *A61B 2017/2926* (2013.01)

(58) Field of Classification Search
CPC ........ A61B 17/22031; A61B 17/00234; A61B 17/0467; A61B 17/10; A61B 17/12; A61B 17/12009; A61B 17/12013; A61B 17/12018; A61B 17/128; A61B 17/1285; A61B 2017/00623; A61B 2017/00349; A61B 2017/1225; A61B 2017/12004; A61B 17/08; A61B 17/0684; A61B 2017/2927; A61B 2017/2926
See application file for complete search history.

(56) References Cited

U.S. PATENT DOCUMENTS

| 5,242,456 | A  | * | 9/1993  | Nash  | A61B 17/0218 606/139 |
| 6,645,205 | B2 | * | 11/2003 | Ginn  | A61B 17/0644 128/200.24 |
| 6,945,978 | B1 | * | 9/2005  | Hyde  | A61B 17/00234 606/142 |
| 2004/0092961 | A1 | * | 5/2004 | Viola | A61B 17/10 606/139 |

(Continued)

*Primary Examiner* — Tuan V Nguyen
(74) *Attorney, Agent, or Firm* — Lerner, David, Littenberg, Krumholz & Mentlik, LLP

(57) ABSTRACT

An apparatus for gathering of tissue of a heart valve leaflet comprises an elongated member and a grasping assembly movable in the elongated member between a retracted position and an extended position. The grasping assembly includes an actuating arm having a proximal end and a distal end. The grasping assembly is attached to the distal end of the activating arm. The grasping assembly is operable to gather and clamp the tissue of the heart valve leaflet such that clamped tissue has a gathered configuration.

10 Claims, 6 Drawing Sheets

(56) References Cited

U.S. PATENT DOCUMENTS

| | | | |
|---|---|---|---|
| 2007/0032807 A1* | 2/2007 | Ortiz | A61B 17/12 606/153 |
| 2008/0249539 A1* | 10/2008 | Stokes | A61B 17/1285 606/142 |
| 2008/0255427 A1* | 10/2008 | Satake | A61B 17/08 600/204 |
| 2008/0319455 A1* | 12/2008 | Harris | A61B 17/0684 606/139 |
| 2009/0318936 A1* | 12/2009 | Harris | A61B 17/0057 606/139 |

* cited by examiner

APPARATUS AND METHOD FOR HEART VALVE REPAIR

CROSS REFERENCE TO RELATED APPLICATIONS

The application claims the benefit of the filing date of the U.S. Provisional Patent Application No. 61/770,612, filed on Feb. 28, 2013, the disclosure of which application is hereby incorporated by reference in its entirety.

BACKGROUND OF THE INVENTION

The present disclosure is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be broken. As a result, the valve does not close normally, and the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to flow back into the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

An embodiment according to the disclosure includes a heart valve repair apparatus includes an elongated member configured for a transcatheter operation and a grasping mechanism including at least first, second, and third fingers, disposed at a distal end of the elongated member and configured to gather a tissue of the heart valve in a generally U-shaped pleat. The apparatus further includes an actuating rod coupled to the grasping mechanism and configured to urge at least the first finger to move away from the second and third fingers, thereby defining an opening within which a heart tissue may be received and to urge the first finger between the second and third fingers to gather the heart tissue in a pleated configuration. The apparatus includes an outer tube movably mounted to the elongated member and having a bore extending therethrough. The outer tube, in a first position thereof, is configured, to substantially enclose a distal end of the elongated member and the grasping mechanism in the bore thereof and, in a second position thereof, to substantially uncover the distal end of the elongated member and the grasping mechanism, thereby deploying the grasping mechanism in an expanded condition for gathering the tissue. The apparatus further includes a clip movably mounted on the elongated member and configured to capture and retain the heart tissue in the pleated configuration.

Another embodiment according to the disclosure includes a clip for mitral valve repair, which clip comprises a generally cylindrical hollow base; and first and second tines extending from said cylindrical base in a generally V-shaped configuration, wherein a recess is defined in said cylindrical base between and adjacent to said first and second tines, and wherein said cylindrical base comprises a raised section extending from said recess to an edge of said cylindrical base distal to said first and second tines. Each of the first and second tines comprises first and second projections, respectively, oriented proximate one another, such that when the first and second projections are urged against a boss, the boss causes the first and second projections to move away from each other.

According to an aspect of the disclosure, a transcatheter method for gathering tissue of a heart valve leaflet includes inserting an elongated catheter assembly to a position adjacent the heart valve leaflet. The catheter assembly comprises an activating arm, and a grasping assembly extending from a distal end of the activating arm. The grasping assembly has a retracted position and an extended position. The method further comprises causing the grasping assembly to deploy from the retracted position to the extended position for gathering the tissue in a gathered configuration. The grasping assembly comprises a plurality of fingers, wherein the plurality of fingers are configured to move away from one another in an expanded configuration thereof and to move toward one another in a collapsed configuration thereof. The catheter assembly further comprises a clip positioned along the activating arm, the clip comprising a generally cylindrical hollow base and first and second tines extending from the generally cylindrical base in a generally V-shaped configuration.

According to an embodiment of the disclosure, a heart valve repair apparatus includes an elongated member configured for a transcatheter operation, a grasping mechanism including at least first, second, and third fingers, disposed at a distal end of the elongated member and configured to gather a tissue of the heart valve in a generally U-shaped pleat, an actuating rod coupled to the grasping mechanism and configured to urge at least the first finger to move away from the second and third fingers, thereby defining an opening within which a heart tissue may be received and to urge the first finger between the second and third fingers to gather the heart tissue in a pleated configuration, an outer tube movably mounted to the elongated member and having a bore extending therethrough, and a clip movably mounted on the elongated member and configured to capture and retain the heart tissue in the pleated configuration. In a first position thereof, the outer tube is configured to substantially enclose a distal end of the elongated member and the grasping member and the grasping mechanism in the bore thereof. In a second position thereof, the outer tube is configured to substantially uncover the distal end of the elongated member and the grasping mechanism, thereby deploying the grasping mechanism in an expanded condition for gathering the tissue.

BRIEF DESCRIPTION OF THE DRAWINGS

Various embodiments of the present disclosure will now be discussed with reference to the appended drawings. It is to be appreciated that these drawings depict only some embodiments of the disclosure and are therefore not to be considered limiting of its scope.

DETAILED DESCRIPTION

As used herein, the terms "proximal" and "distal" are to be taken as relative to a user (e.g., a surgeon or an interventional cardiologist) using the disclosed transcatheter devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 2:
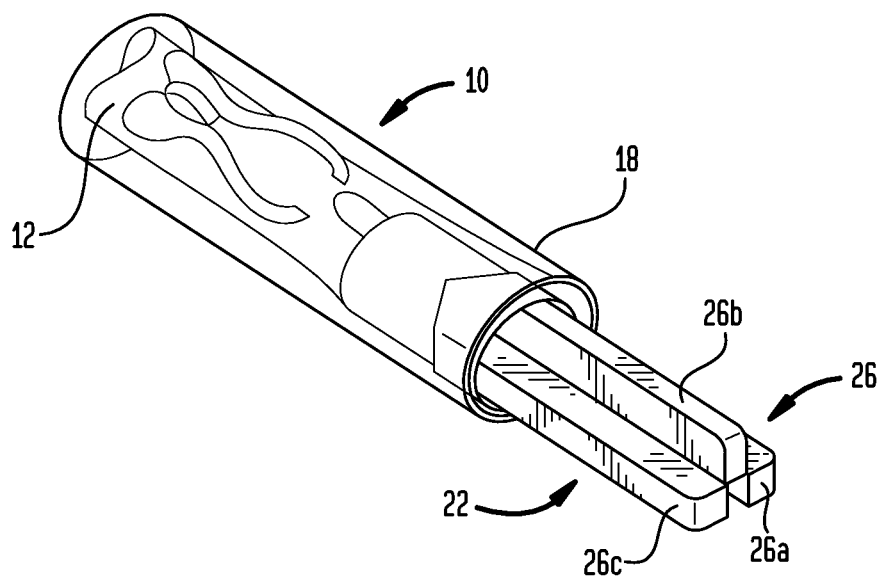
FIG. 2 is a perspective view of the distal end of a device for heart valve repair according to an embodiment, the device being in a collapsed configuration.
Figure 3:
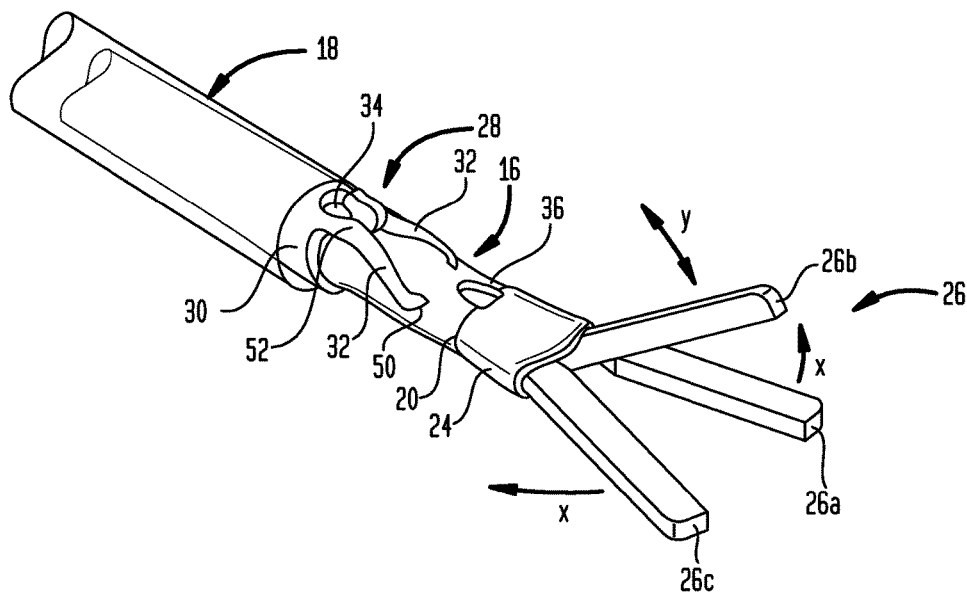
FIG. 3 is a perspective view of the device of FIG. 2 in an expanded configuration.
Figure 4:
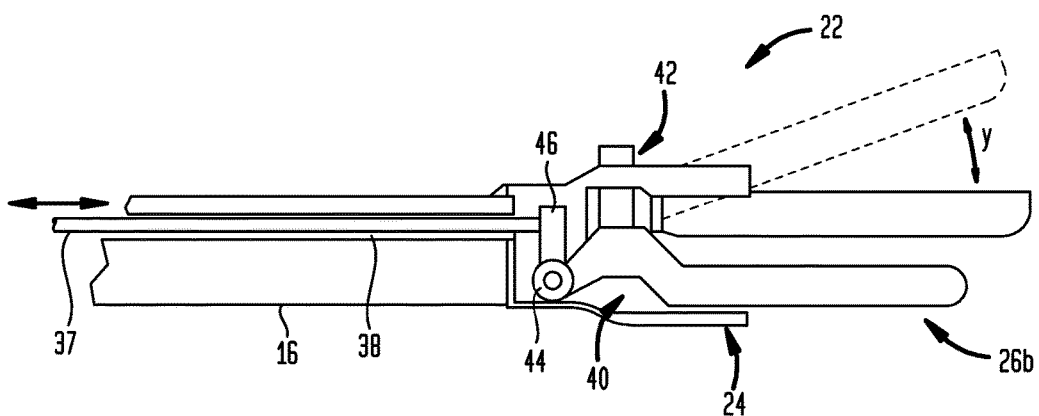
FIG. 4 is a longitudinal cross-sectional view of the distal end of the device of FIG. 2.
Figure 5:
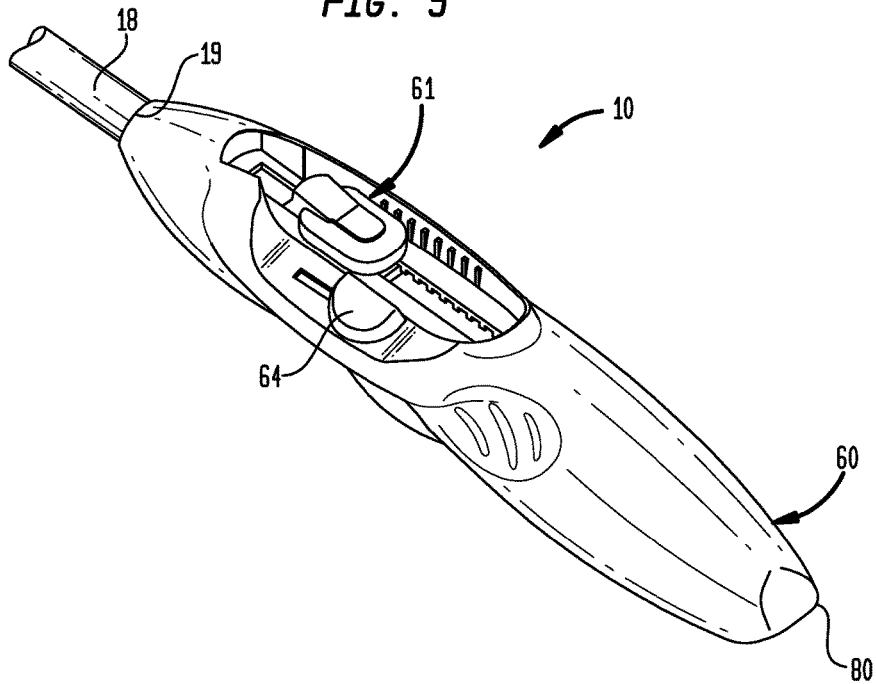
FIG. 5 is a perspective view of a handle for the device of FIG. 2.
Figure 6:
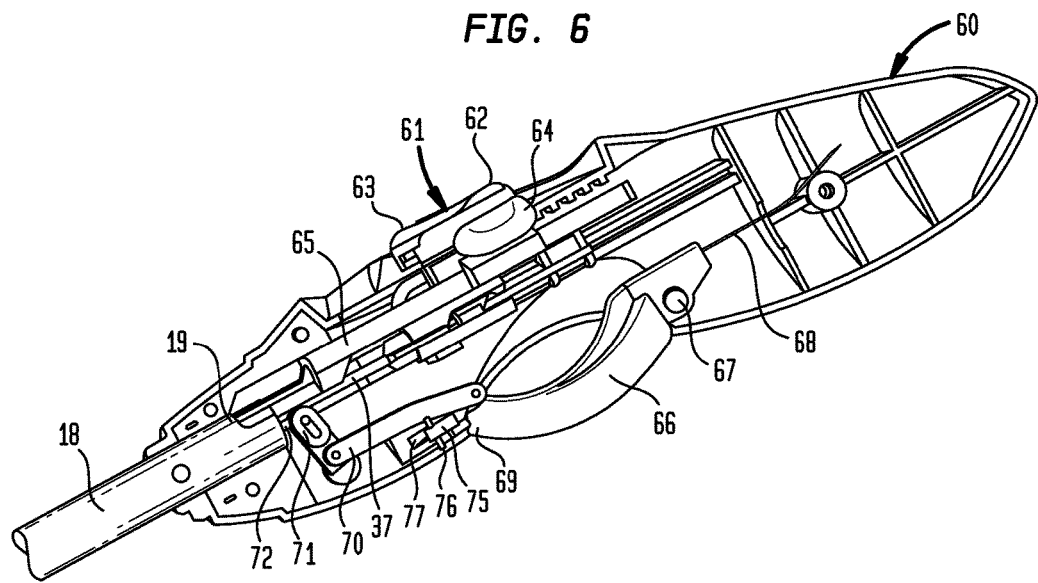
FIG. 6 is a longitudinal cross-sectional view of the handle of FIG. 5.
Figure 7:
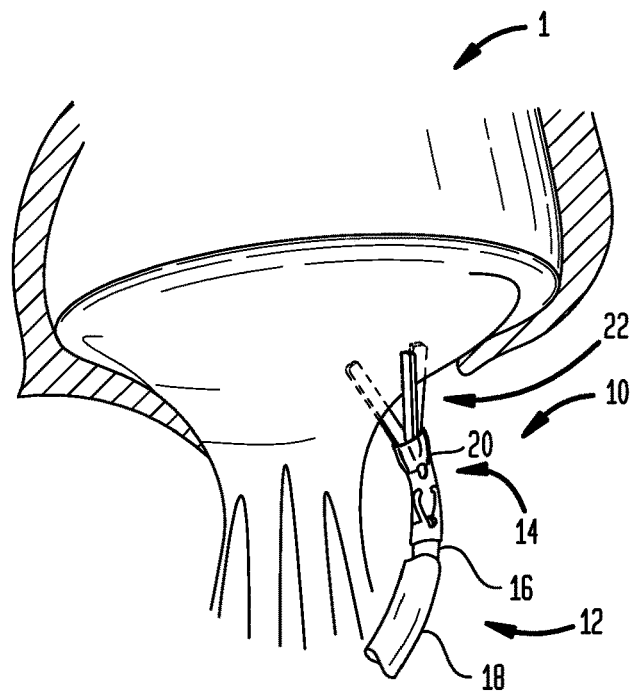
FIG. 7 is a highly schematic perspective view showing the use of the device of FIG. 2 to repair a heart valve leaflet.
Figure 8:
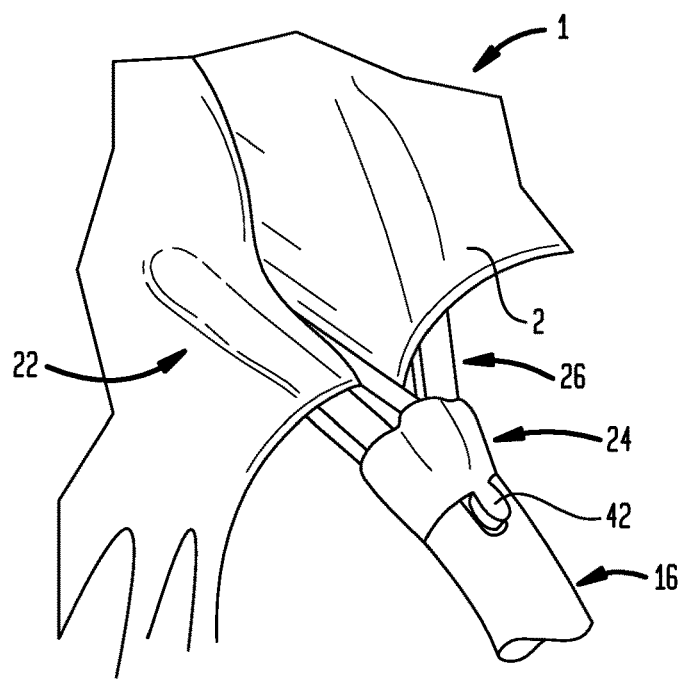
FIG. 8 is a highly schematic enlarged perspective view of the grasping mechanism of the device of FIG. 2 gathering the tissue of a heart valve.
Figure 9:
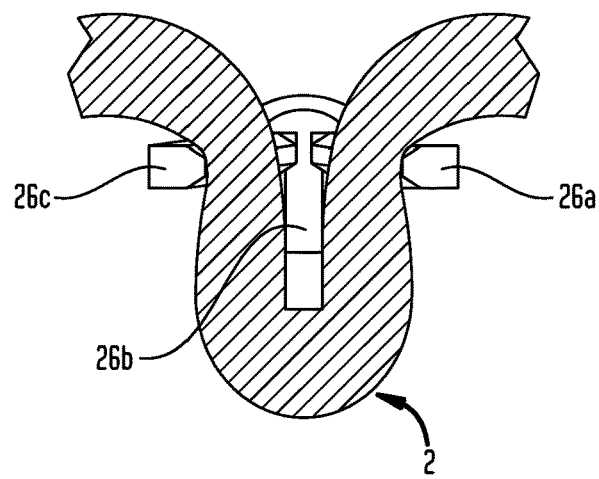
FIG. 9 is a cross-sectional end view of the heart valve tissue gathered by the device of FIG. 2 to form a generally U-shaped pleat.
Figure 10:
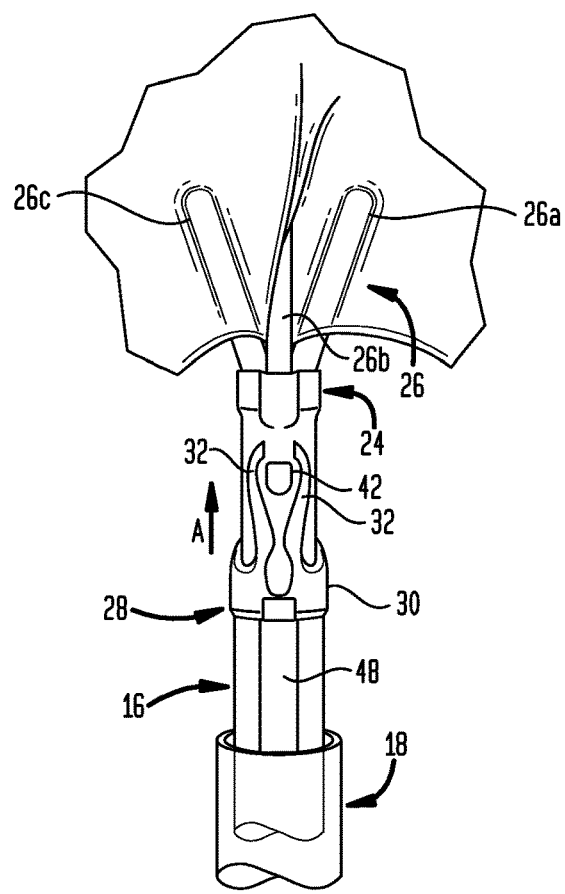
FIGS. 10-12 are perspective views showing the use of the device of FIG. 2 to deploy a clip for clamping or capturing the tissue in the gathered configuration.
Figure 11:
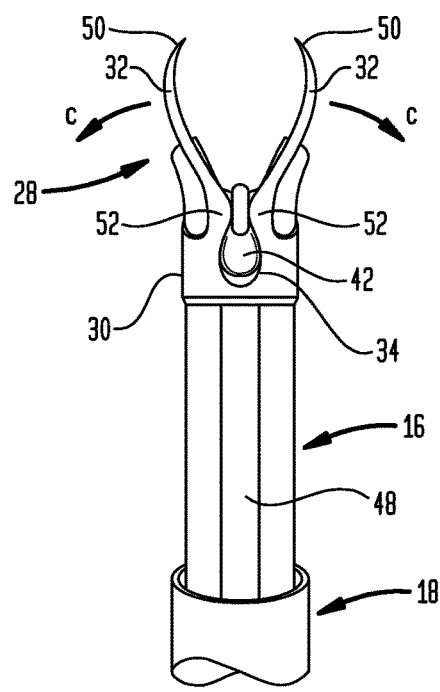
Figure 12:
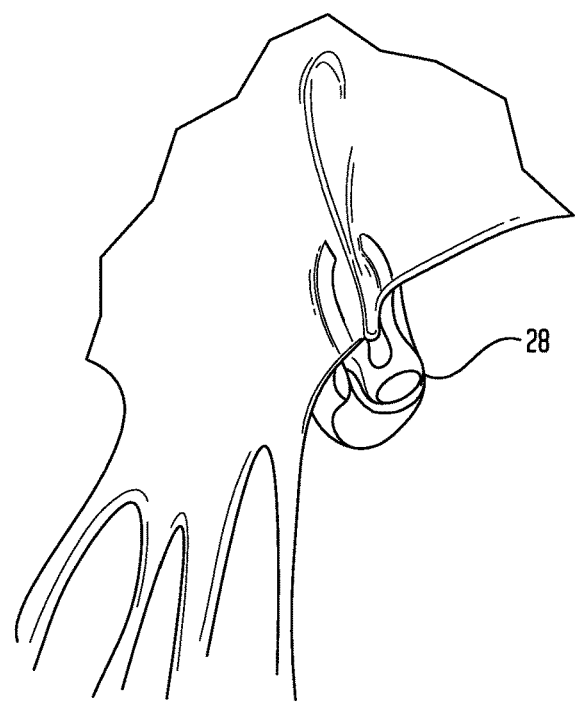

Described below are an apparatus and method for heart valve repair. FIGS. 2 and 3 illustrate the grasping mechanism 22 in a retracted and a deployed configuration, respectively, whereas FIG. 4 illustrates a cross-sectional view of the grasping assembly 23. FIGS. 5 and 6 illustrate two different views of the handle 60 configured for controlling and operating the heart repair apparatus. FIGS. 7-9 illustrate various operational stages of the grasping mechanism 22 while gathering the tissue. FIGS. 10-11 illustrate the deployment of the clip 28 to capture the tissue gathered by the grasping mechanism 22. Finally, FIG. 12 illustrates the clip 28 having captured the tissue in a gathered configuration, thereby reducing the prolapse in the heart tissue. The various elements of the apparatus and the operational stages of the apparatus are described in further detail below.

Figure 1:
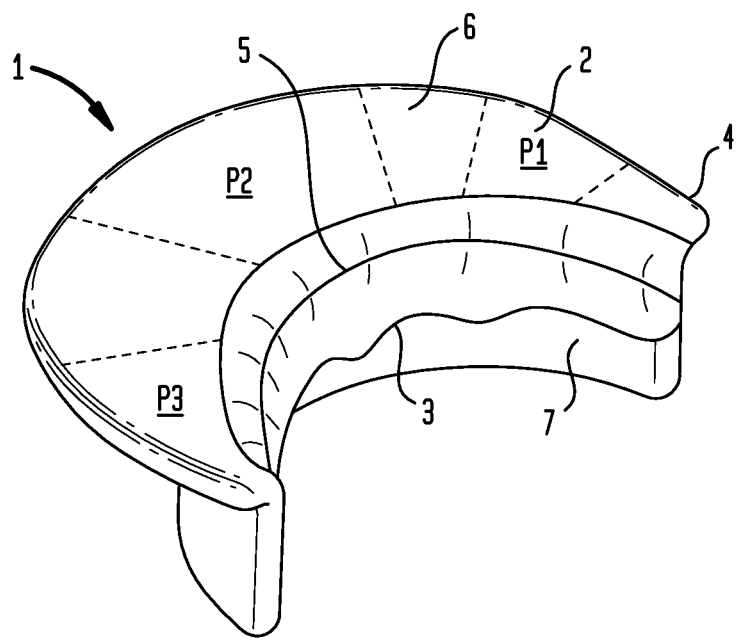
FIG. 1 is a diagrammatic perspective view of the posterior leaflet of a mitral valve.

Referring to FIG. 1, an exemplary mitral valve 1 includes posterior leaflet 2 and anterior leaflet 3. Leaflets 2 and 3 extend from annulus 4 to coaptation line 5 where the leaflets meet. Posterior leaflet 2 has upper portion 6 that is generally perpendicular to the direction of blood flow through valve 1 and extends between annulus 4 and coaptation line 5. Additionally, posterior leaflet 2 has lower portion 7 that is generally parallel to the direction of blood flow through valve 1 and that extends below coaptation line 5. Chordae tendineae (not shown) may connect lower portion 7 of posterior leaflet 2 to the papillary muscles (not shown) of the left ventricle (not shown). Posterior leaflet 2 has three scalloped portions P1, P2, and P3, any of which may include a portion that is billowed, loose, or floppy, and which therefore may be the cause of a prolapse condition of the valve. The inventive devices, systems, and methods described herein may be adapted to repair such a billowed, loose, or floppy portion of posterior leaflet 2 or anterior leaflet 3.

Referring to FIGS. 2-4, the distal portion of an exemplary device 10 for transcatheter gathering of heart valve leaflet tissue includes elongated catheter assembly 12 adapted to be inserted through the apex of a human heart so that distal portion 14 of the catheter assembly may reach the patient's mitral valve 1 for repair thereof. Catheter assembly 12 includes outer elongated tube 18 and grasping assembly 23 slidably disposed within the outer tube. Grasping assembly 23 includes elongated actuating rod 37 and grasping mechanism 22 attached to distal end 20 of the actuating rod, as seen in FIG. 4. Grasping assembly 23 is longitudinally slidable within outer tube 18 between an initial or retracted position (not shown) in which grasping mechanism 22 lies within the outer tube and a deployed position (FIG. 3) in which the grasping mechanism protrudes distally beyond the distal end of the outer tube. As discussed in detail below, grasping mechanism 22 can grasp and fold at least a portion of leaflet 2. Outer tube 18 or one or more of the components forming distal portion 14 of catheter assembly 12 may be wholly or partly made of one or more echogenic materials so that device 10 can be more easily visualized inside a patient using three-dimensional echocardiography.

As seen in FIGS. 2-4, grasping assembly 23 includes coupler 24 attached to distal end 20 of elongated member 16 which is slidably received within outer tube 18. Coupler 24 mechanically connects actuating rod 37 to a plurality of fingers 26, which define grasping mechanism 22. Fingers 26 extend distally from coupler 24 and are pivotably connected to the coupler so as to move between a collapsed configuration (FIG. 2) and an expanded configuration (FIG. 3).

In an exemplary embodiment, grasping mechanism 22 may include three fingers 26a, 26b, and 26c. It is noted here that other embodiments may include more than three fingers, for example, four fingers or five fingers as well. Three fingers 26a, 26b, and 26c are capable of moving relative to one another to provide a space therebetween for gathering the tissue of the heart valve leaflet. For example, upon movement of outer tube 18 relative to grasping assembly 23, thereby exposing grasping assembly 23, fingers 26a, 26b and 26c may move outwardly away from one another. On the other hand, when outer tube 18 is moved distally relative to grasping assembly 23 (or the grasping assembly is retracted proximally relative to the outer tube) to place the grasping assembly in a retracted position, as partially shown in FIG. 2, distal end of the outer tube 18 contacts fingers 26 and urges them toward one another until fingers 26 achieve the collapsed configuration. Once fingers 26 are in the collapsed configuration, grasping assembly 23 may be retracted fully into outer tube 18.

In the collapsed configuration, fingers 26 are immediately adjacent and substantially parallel to one another so as to occupy a minimum transverse cross-section, allowing confinement within outer tube 18. This enables fingers 26 to slide into outer tube 18 in the retracted position. On the other hand, when outer tube 18 is retracted proximally relative to grasping assembly 23 (or the grasping assembly is advanced distally relative to the outer tube) to place grasping mechanism 22 in the deployed position, fingers 26 move outwardly away from one another to the expanded configuration having a much larger transverse cross-section. A spring or other biasing element (not shown) disposed within coupler 24 (or between fingers 26) may bias at least fingers 26a and 26c toward their expanded condition, in which fingers 26a and 26c diverge from each other in a generally "V-shaped" configuration. The angle between fingers 26a and 26c in the expanded condition may be an acute angle. Finger 26b, which is disposed between fingers 26a and 26c, may move from its retracted position to its expanded position upon actuation of grasping assembly 23.

With reference to FIG. 4, finger 26b is attached to actuating rod 37 at least partially disposed within elongated member 16. Specifically, actuating rod 37 is positioned in bore 38 extending through elongated member 16 and can move longitudinally relative to the elongated member between a retracted position and an actuated position. Since actuating rod 37 is attached to finger 26b, moving the actuation rod away from grasping mechanism 22 urges finger 26b in the direction of arrow y to move from the collapsed condition to the expanded condition, as shown in phantom. Conversely, moving actuating rod 37 toward grasping mechanism 22 causes finger 26b to move to the collapsed position illustrated in FIG. 4.

Catheter assembly 12 may include biocompatible clip 28 slidably mounted on the distal end of elongated member 16 and adapted for application to a tissue, such as the tissue of leaflet 2. Clip 28 may include generally cylindrical base 30 sized to be assembled in friction fit around elongated member 16 and a plurality of tines 32 protruding from the cylindrical base. When clip 28 is positioned on elongated member 16, tines 32 may rest on the outer surface of the elongated member. Clip 28 may include first and second tines 32 oriented at an acute angle relative to one another, e.g., in a generally V-shaped configuration. Clip 28, or at least tines 32, may be wholly or partly made of a resilient material. Free ends 50 of tines 32 may be sharp in order to pierce tissue. In an exemplary embodiment, tines 32 may further or alternatively include features such as teeth or barbs (not shown) along the inner edges for holding clip 28 to the tissue captured therebetween. In the illustrated embodiment, tines 28 are curved towards tips 50, in which case the clamping force of clip 28 is concentrated as a compressive force at the tips. In another embodiment, tines 32 may comprise uniform or flat inner edges, wherein the tines would exert a generally uniform force over the entire area of the captured tissue. Tines 32 may be configured to diverge from each other such that free ends 50 of tines 32 may expand to a width generally equal to the width between the free ends of fingers 26a, 26c in their expanded condition. In an exemplary embodiment, tines 32 may have a length generally equal to the length of fingers 26. It is noted here that the longer the tines 32, the farther away from base 30 is the contact with the tissue, thereby lessening the mechanical advantage of clip 28 holding the tissue. The appropriate length of tines 32 may be determined by material properties of the material from which clip 28 is made and the desired force to hold the tissue.

As is seen more clearly in FIGS. 10 and 11, tines 32 of clip 28 are spaced from one another at their connection to base 30 of the clip so as to define recess 34 between them. Recess 34 is sized to receive boss 42 that projects radially from connection segment 40 (FIG. 4) as described in detail below. Coupler 24 further has hole 36 sized to receive boss 42 (FIG. 3). Base 30 further includes outwardly raised section 35 (FIG. 11) extending from recess 34 to an edge of the base. Raised section 35 is sized to slide over boss 42.

With continued reference to FIGS. 10 and 11, catheter assembly 12 further includes shaft 48 positioned along elongated member 16. In some embodiments, shaft 48 may be disposed on the top of elongated member 16. Regardless, shaft 48 can move longitudinally relative to elongated member 16 and is in contact with clip 28 when clip 28 has not been deployed. Specifically, shaft 48 may be adapted to contact cylindrical base 30 of clip 28 and, consequently, can urge clip 28 forward in the direction indicated by arrow A when shaft 48 is moved toward fingers 26 of catheter assembly 12.

In accordance with another embodiment, actuation rod 37 may be attached to finger 26b through connection segment 40. Boss 42 extends substantially perpendicular from a middle portion of connection segment 40 and may protrude out through hole 36 (FIG. 3) of coupler 24 in certain predetermined positions of finger 26b, as set forth in detail below. In the retracted position of fingers 26a, 26b, and 26c, boss 42 is generally flush with the outer diameter of elongated member 16. Roller 44 may be connected to an end of connection segment 40 and is adapted to roll along the inner surfaces of coupler 24. Bar 46 may extend substantially vertically from roller 44 and may be directly connected to actuating rod 37. These components of connection segment 40 may be formed as a one-piece integral body.

As described in detail below, moving actuating rod 37 away from coupler 24 causes roller 44 to roll toward the free end of the coupler. In turn, this motion of roller 44 urges finger 26b to pivot upwardly to the expanded condition as shown in phantom in FIG. 4. In addition, when roller 44 rolls toward the free end of coupler 24, boss 42 moves downwardly through hole 36 in the coupler. On the other hand, moving actuating rod 37 in the opposite direction towards the free end of coupler 24 causes roller 44 to roll away from the free end of the coupler. When roller 44 rolls away from the free end of coupler 24, boss 42 moves upwardly so as to project out from hole 36. This motion of roller 44 urges finger 26b to pivot downwardly to the collapsed condition shown in FIG. 4. Further motion of roller 44 away from the free end of coupler 24 causes finger 26b to pivot downwardly to a deployed configuration shown in FIGS. 8 and 9, for example. In the deployed configuration boss 42 extends out from hole 36.

With reference to FIGS. 5 and 6, device 10 further includes handle 60 at proximal end 19 of outer tube 18. Handle 60 may include first button 61 for controlling actuating rod 37, second button 64 for controlling outer tube 18, and third button 66 for deploying clip 28.

First button 61 is moveable longitudinally relative to handle 60 and to second button 64. First button 61 may be attached to actuating rod 37, such that sliding movement of first button 61 in a proximal or distal direction results in a corresponding sliding movement of actuating rod 37.

Second button 64 may be moveable longitudinally relative to handle 60 for controlling the movement of outer tube 18 relative to elongated member 16. Second button 64 may be attached to one end of linkage 65, the other end of which may be attached to outer tube 18, such that sliding movement of second button 64 in a proximal or distal direction results in a corresponding sliding movement of outer tube 18.

Third button 66 may have a trigger shape and may be connected at one end to handle 60 by pivot pin 67 that allows for movement of third button 66 in a lateral direction relative to the longitudinal axis of handle 60 for controlling the movement of shaft 48 (FIG. 10) relative to outer tube 18. Spring 68 may bias third button 66 to return to its initial position after third button 66 has been actuated. Opposite end 69 of third button 66 may be pivotally coupled to a linkage assembly including first linkage 70, second linkage 71, and third linkage 72, all of which are pivotally connected to one another in series. Third linkage 72 may be attached to a proximal end of shaft 48, such that actuation of third button 66 may cause third linkage 72 to slide proximally to urge shaft 48 distally and thereby deploy clip 28.

A description of the use of catheter assembly 12 now follows in accordance with one embodiment of the invention. With reference to FIGS. 7-12 illustrating various stages of deployment of catheter assembly 11, the catheter assembly may be used to repair a heart valve, such as mitral valve 1. Catheter assembly 12 may be introduced into a patient using any known procedures. For example, the user may insert at least the distal end of catheter assembly 12 percutaneously using the femoral approach. Preferably, catheter assembly 12 may be inserted into a patient's body with grasping mechanism 22 in the collapsed configuration (FIG. 2). Once the distal end of catheter assembly 12 has reached the desired site (i.e., adjacent leaflet 2) grasping mechanism 22 may be deployed to its expanded configuration (FIG. 3). As discussed above, to deploy grasping mechanism 22 from the collapsed configuration (FIG. 2) to the expanded configuration (FIG. 3), outer tube 18 is moved proximally (i.e., toward handle 60) relative to elongated member 16 to its retracted position. In an exemplary embodiment, the user may move outer tube 18 to the retraced position by moving second button 64 toward free end 80 of handle 60.

When outer tube 18 is in the retraced position, at least fingers 26a and 26c automatically move laterally away from finger 26b (FIG. 3) in the direction indicated by arrows X and define a first plane. Fingers 26a and 26c form an angle therebetween. Finger 26b may also move automatically in the direction indicated by arrow Y upon movement of outer tube 18 to the retracted position. Alternatively, finger 26b may move in the direction indicated by arrow Y by moving actuating rod 37 toward handle 60. To move actuating rod 37 toward handle 60, the user may move first button 61 toward free end 80 of handle 60. Finger 26b, thus, pivotally moves in a plane generally perpendicular to the first plane defined by fingers 26a and 26c, in an exemplary configuration.

Once grasping mechanism 22 is in the expanded configuration, fingers 26 of catheter assembly 12 may be placed surrounding at least a portion of leaflet 2, as shown in FIGS. 8 and 10. Fingers 26a and 26c are generally on one side of the tissue of leaflet 2, whereas finger 26b is on the opposing side of the tissue of the leaflet. Finger 26b is then pivoted about coupler 24 beyond the first plane defined by fingers 26a and 26c to gather or capture tissue therebetween and form a substantially U-shaped pleat in the captured tissue, as seen in FIG. 9. Simultaneously, boss 42 projects out of hole 36. In other embodiments, for example, one having four fingers, the captured tissue would form a sideways S-shaped fold and one having five fingers, the captured tissue would form a W-shaped fold.

Clip 28 may then be deployed to hold the captured tissue in the substantially U-shaped pleated gathered configuration. To deploy clip 28, the user may actuate third button 66. Upon actuation of third button 66, shaft 48 moves toward fingers 26. As shaft 48 moves forward, it urges clip 28 toward fingers 26.

With reference to FIG. 11, as clip 28 is being deployed, bases 52 of tines 32 contact boss 42 projecting out from hole 36, causing tines 32 to move away from each other in the direction indicated by arrows C, as clip 28 is being urged distally by shaft 48. With tines 32 in an expanded position, clip 28 captures tissue between the tines with each of the tines on the opposite sides of the tissue gathered in the U-shaped pleat. As clip 28 continues to move distally, boss 42 is positioned within recess 34 and bases 52 no longer contact the boss. As bases 52 of tines 32 are no longer subject to the forces exerted by boss 42, the tines of clip 28 move toward each other and secure the captured tissue in the substantially U-shaped pleat or gathered configuration. Thus, the loose or floppy tissue in leaflet 2 is gathered and secured by clip 28, thereby mitigating a cause of the prolapsed condition of the valve.

Once clip 28 has secured the tissue of leaflet 2, finger 26b is retracted from its deployed position to assume its retracted position. As finger 26b pivots upwardly from the retracted position, boss 42 is retracted into elongated member 16 through hole 36. The retraction of boss 42 facilitates the proximal movement of elongated member 16 relative to clip 28. Clip 28 is attached to the tissue captured therewithin. Grasping mechanism 22 is gradually withdrawn away from the captured tissue into outer tube 18. As grasping mechanism 22 is gradually withdrawn, fingers 26 are urged toward their collapsed configuration by cylindrical base 30, through which coupler 24 and fingers 26 are withdrawn. At the same time, outer tube 18 may be moved distally (i.e., away from handle 60) relative to elongated member 16 to its deployed position. As outer tube 18 moves to its deployed positions, it encloses elongated member 16 and fingers 26 in the collapsed condition. Catheter assembly 12 may then be completely withdrawn from clip 28, leaving clip 28 secured to the tissue of valve 2.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Although the disclosure herein has been described with reference to particular embodiments in which the catheter assembly is inserted into the patient via an introducer and through the apex of the heart (i.e., transapical insertion), it is to be understood that the disclosure contemplates embodiments in which the catheter assembly extends through a portion of the vasculature of the patient to reach the heart, for example, through a transfemoral or subclavian artery. In such embodiments, some of the device components may have to be oriented in a different direction to that described herein. For example, the disclosure contemplates embodiments in which the distal portion of the catheter assembly approaches the mitral valve from the upstream side as well as from the downstream side of the valve.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An apparatus for gathering tissue of a heart valve leaflet, the apparatus comprising:
    an outer tube;
    an elongated member slidably received within the outer tube; and
    a grasping assembly movable in the outer tube between a retracted position and an extended position, the grasping assembly including an actuating rod having a proximal end and a distal end and a plurality of fingers extending from the distal end of the actuating rod;
    wherein the grasping assembly is disposed at a distal end of the elongated member, the grasping assembly being operable to gather and clamp the tissue of the heart valve leaflet such that the clamped tissue has a gathered configuration,
    wherein, in the extended position, a first and a second of said plurality of fingers diverge from one another, thereby forming an angle therebetween and defining a first plane, and a third of said plurality of fingers is pivotable about the distal end of the elongated member in a plane generally perpendicular to the first plane, the grasping assembly having a first operating position in which the third of said plurality of fingers is positioned on one side of the first plane and a second operating position in which the third of said plurality of fingers is positioned on another side of the first plane.

2. The apparatus according to claim 1, further comprising a clip slidably mounted to the distal end of the elongated member.

3. The apparatus according to claim 2, wherein the clip comprises:
    a generally cylindrical hollow base; and
    first and second tines each having a base and extending from the generally cylindrical hollow base in a generally V-shaped configuration.

4. The apparatus according to claim 3, wherein the clip further defines a recess in the generally cylindrical hollow base adjacent to and between the bases of the first and second tines.

5. The apparatus according to claim 4, further comprising a connector having a boss configured to urge the first and second tines away from one another; and wherein the recess is configured to accommodate the boss.

6. The apparatus according to claim 4, wherein the clip further comprises a raised section projecting radially outward from the generally cylindrical hollow base and positioned between the first and second tines.

7. The apparatus according to claim 2, further comprising a shaft for urging the clip toward the distal end of the elongated member.

8. The apparatus according to claim 7, wherein the outer tube is configured to encase said actuating rod, the outer tube in a first position encasing said plurality of fingers in the collapsed configuration, and, the outer tube in a second position uncovering said plurality of fingers.

9. The apparatus according to claim 8, further comprising a handle for operating the apparatus, the handle comprising:
    a first button for actuating the third finger between a collapsed configuration and an expanded configuration;
    a second button for actuating the outer tube between the first position and the second position; and
    a third button for actuating the shaft for urging the clip toward the distal end of the elongated member.

10. A heart valve repair apparatus comprising:
    an elongated member configured for a transcatheter operation;
    a grasping mechanism comprising at least first, second, and third fingers disposed at a distal end of said elongated member and configured to gather tissue of the heart valve in a generally U-shaped pleat, the second and third fingers defining a first plane;
    an actuating rod coupled to the grasping mechanism and configured to urge at least the first finger to pivot away from a first side of the first plane along a second plane generally perpendicular to the first plane, thereby defining an opening within which the tissue may be received, and configured to urge the first finger along the second plane between the second and third fingers to a second side of the first plane to gather the heart tissue in a pleated configuration;
    an outer tube movably mounted to said elongated member and having a bore extending therethrough,
    wherein the outer tube in a first position substantially encloses the distal end of the elongated member and the grasping mechanism in the bore, and in a second position substantially uncovers the distal end of the elongated member and the grasping mechanism, thereby deploying the grasping mechanism in an expanded condition for gathering the heart tissue, and
    a clip movably mounted on the elongated member and configured to capture and retain the heart tissue in the pleated configuration.

* * * * *